(12) United States Patent  (10) Patent No.: US 6,458,104 B2
Gautsche  (45) Date of Patent: Oct. 1, 2002

(54) IV ADMINISTRATION LINES FASTENING AND IDENTIFICATION DEVICE

(75) Inventor: Julie K. Gautsche, Hayward, WI (US)

(73) Assignee: William E. Gautsche, Jr., Hayward, WI (US)

( * ) Notice: Subject to any disclaimer, the term of this patent is extended or adjusted under 35 U.S.C. 154(b) by 38 days.

(21) Appl. No.: 09/785,984

(22) Filed: Feb. 20, 2001

Related U.S. Application Data

(60) Provisional application No. 60/188,828, filed on Mar. 13, 2000.

(51) Int. Cl.[7] .............................................. A61M 5/32
(52) U.S. Cl. ................... 604/179; 604/80; 128/DIG. 6; 128/DIG. 26; 248/68.1; 248/74.1; 248/75
(58) Field of Search ............................. 604/80, 93.01, 604/174, 178, 179, 180, 258, 539; 128/DIG. 6, DIG. 26; 248/68.1, 74.1–74.5, 75, 80, 89, 90; 211/60.1

(56) References Cited

U.S. PATENT DOCUMENTS

| 3,747,166 | A | * | 7/1973 | Erossd ................... 248/229.26 |
| D243,477 | S | | 2/1977 | Cutruzzula et al. |
| 4,088,136 | A | | 5/1978 | Hasslinger et al. |
| 4,167,211 | A | | 9/1979 | Haller |
| D260,850 | S | | 9/1981 | Greenblatt |
| D263,624 | S | | 3/1982 | Stenzler et al. |
| D265,508 | S | | 7/1982 | Rustebert |
| 4,397,641 | A | | 8/1983 | Jacobs |
| 4,453,933 | A | | 6/1984 | Speaker |
| D290,041 | S | | 5/1987 | Scott |
| 5,085,326 | A | * | 2/1992 | Russell et al. ................... 211/4 |
| 5,112,312 | A | * | 5/1992 | Luther .......................... 451/24 |
| 5,209,441 | A | * | 5/1993 | Satoh ................... 128/DIG. 26 |
| 5,224,674 | A | | 7/1993 | Simons |
| 5,226,892 | A | * | 7/1993 | Boswell ...................... 174/135 |
| 5,316,246 | A | | 5/1994 | Scott et al. |
| 5,336,179 | A | | 8/1994 | Ryan |
| 5,389,082 | A | * | 2/1995 | Baugues et al. ..... 128/DIG. 26 |
| 5,876,371 | A | | 3/1999 | Yokoyama et al. |
| 5,974,708 | A | | 11/1999 | Webb et al. |
| 6,315,759 | B1 | * | 11/2001 | Peterson .................... 248/68.1 |

* cited by examiner

Primary Examiner—Lesley D. Morris
Assistant Examiner—Patrick Buechner
(74) Attorney, Agent, or Firm—Tipton L. Randall (57) ABSTRACT

An intravenous administration lines fastening and identification device includes a hollow cylindrical fastening member of resilient, flexible material. The cylindrical member has a full length longitudinal slit aperture. A plurality of tube holding members of resilient, flexible material, each with a cylindrical bore, are secured to the outer surface of the hollow cylindrical fastening member opposite the fastening member longitudinal slit aperture. Each tube holding member bore axis is oriented perpendicular to the fastening member longitudinal cylindrical axis. The tube holding members each have a full length slit aperture opposite the fastening member, with the slit aperture accessing the holding member cylindrical bore. An identification marking surface is present on the cylindrical member outer surface in register with and adjacent each tube holding member for identification of the IV tubing contents.

17 Claims, 5 Drawing Sheets

IV ADMINISTRATION LINES FASTENING AND IDENTIFICATION DEVICE

CROSS-REFERENCE TO RELATED APPLICATIONS, IF ANY

This application claims the benefit under 35 U.S.C. §119 (e) of co-pending provisional application Serial No. 60/188,828, filed Mar. 13, 2000. Application Serial No. 60/188,828 is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to a device for organizing and securing several IV lines together, and more particularly, to a device for organizing, securing and identifying a plurality of IV tubes in conjunction with an exterior structure.

2. Background Information

The subject matter of this invention is directed primarily to flexible lines in the form of fluid-conducting tubes that are commonly used within the medical profession. It is common medical practice to treat and medicate a patient by introducing therapeutic agents, drugs, medications, nutrients, and various other liquids directly into the blood stream of the patient through systems commonly known as intravenous (IV) administration systems. Often a critically ill patient will require several such systems concurrently operative to proved different treatment agents. Additionally, catheters are frequently utilized to monitor body functions. Many of these catheters, IV tubes, and other monitoring lines are placed on the patient even prior to transportation of the patient from a surgery area to a convalescing area.

Common features of presently used intravenous administration systems include the need for maintaining sterility of the component elements up to the time of installation to the patient. Minimization of all risks of infection is paramount, since the typical patient usually has enough adverse conditions without adding any through mishandling or contamination of the intravenous administration system. The IV tubing is normally available in acute sickrooms in the form of prepackaged, sterile lengths, with attached sterile needles. For acutely ill patients, time cannot usually be spared to enable trimming IV component lengths for neatness. The entire tubing length is utilized, even if such excess length results in adding a significant length portion to a tangle of tubing from other intravenous administration system. Quickly, the presence of numerous lines can result in a situation where the health care professional caring for the patient will lose direct cognizance of the specific contents of each intravenous administration system unless reference is made to the identification of the corresponding supply reservoirs.

Further, at times certain medications are injected into a fluid line. Extreme care must be exercised to ensure that the right medication is being injected into the correct line. The problem of confusing IV lines and catheters entering a patient's body is accentuated under emergency conditions. There is the further problem of various lines physically interacting with one line causing another line to become disconnected. The foregoing problems increase the risk of patient injury by either infusing medicine or blood at the wrong entry site, or by failure to infuse needed medications.

The entanglement of numerous IV and catheter lines is exceedingly common in the hospital room while the patient is recovering from a surgical operation. This entanglement is caused primarily by the patient moving around in either a conscious or unconscious state. There is a need within the hospital room for a device to which the different lines that are connected to the patient can be located, with the device keeping the different lines separate and unentangled and also making identification of each line readily apparent to the physicians and nurses attending the patient. The device should also be easily transportable with the IV reservoirs as the patient moves from location to location.

In U.S. Pat. No. 4,088,136 Hasslinger et al. disclose a strap fastener that loops around a catheter tube with the strap then encircling the leg of a patient or other support to anchor the catheter tube.

U.S. Pat. No. 4,167,211 by Haller describes an interlocking spacer for holding multiple layers of coiled tubes in a specific orientation. The spacer has an elongated body with U-shaped seats to hold the tubes and dovetail formations to interconnect multiple spacers.

Jacobs, in U.S. Pat. No. 4,397,641 discloses a catheter support device for anchoring an intravenous catheter and a portion of associated tubing to the patient. A rigid annular support is adhesively secured to the patient. An inclined catheter bracket holds the catheter and an arcuate passageway in the support mechanically isolates the tubing from the catheter.

U.S. Pat. No. 4,453,933 by Speaker describes an adjustable strap with fastening means for securing around a patient's limb. The strap has clamps or posts for securing IV lines to the strap. A protective sleeve that covers the patient's limb interlocks with the strap device.

In U.S. Pat. No. 5,224,674 Simons discloses a device for organizing IV administration lines. The device has a plurality of individual passages for IV lines and is removably attachable to appropriate support structures near a patient. The box-like structure has a hinged lid with internal passages for the IV lines.

U.S. Pat. No. 5,316,246 by Scott describes an intravenous tube holder which has a plurality of clips along one edge for securing the holder to an IV tube. On the opposite edge is provided a writing surface for identifying the IV tube or giving instructions. The tube holder has interlocking ends for interconnection of multiple holders.

Ryan, in U.S. Pat. No. 5,336,179 describes an IV line organizer with a block having passages for the IV lines. The block is connected to a clamping system for securing the device to an object.

U.S. Pat. No. 5,876,371 by Yokoyama et al. shows an IV tube holder with tracks for the tubing and a writing surface for identification of the tubing contents. The holder has interlocking ends for interconnection of multiple holders. The device is fastened to a support with a C-clamp.

Webb, in U.S. Pat. No. 5,974,708, discloses an intravenous line identification system that includes a set of tags, each of unique color, with the tags of the set attachable around intravenous lines. One tag is secured to each IV line in use and only then is the tag divided and moved adjacent the medicinal source and line output. The corresponding unique color of the divided tag allows quick and positive identification of each line by health care workers.

Some examples of tube anchors and tube holders for which design patents have been granted include U.S. Pat. No. Des. 243,850 by Cutruzzula et al.; U.S. Pat. No. Des. 260,850 by Greenblatt; U.S. Pat. No. Des. 263,624 by Stenzler et al; U.S. Pat. No. Des. 265,508 by Rusteberg; and U.S. Pat. No. Des. 290,041 by Scott. None of these design patents shows the outward features of the IV administration lines fastening and identification device of the present invention.

SUMMARY OF THE INVENTION

The invention is an intravenous administration lines fastening and identification device. The device includes a hollow cylindrical fastening member of resilient, flexible, polymeric, resinous material. The cylindrical member has inner and outer surfaces and a cylindrical bore with a longitudinal cylindrical axis there through. The cylindrical member has a full length longitudinal slit aperture accessing the cylindrical bore. A plurality of tube holding members of resilient, flexible, polymeric, resinous material, each with a cylindrical bore and longitudinal bore axis, are secured to the outer surface of the hollow cylindrical fastening member opposite the fastening member longitudinal slit aperture. Each tube holding member longitudinal bore axis is oriented perpendicular to the fastening member longitudinal cylindrical axis. The tube holding members each have a full length longitudinal slit aperture opposite the fastening member, with the slit aperture accessing the holding member cylindrical bore. An identification marking surface is present on the cylindrical fastening member outer surface in register with and adjacent to each tube holding member secured thereto.

DESCRIPTION OF THE PREFERRED EMBODIMENTS

Nomenclature

10 Fastening and Identification Device
15 Hollow Cylindrical Fastening Member
20 Inner Surface of Fastening Member
25 Outer Surface of Fastening Member
27 Cylindrical Bore of Fastening Member
30 Longitudinal Slit Aperture of Fastening Member
35 Beveled Edges of Slit Aperture
40 Tube Holding Members
45 Cylindrical Bore of Tube Holding Member
50 Longitudinal Slit Aperture of Tube Holding Member
55 Beveled Edge of Slit Aperture
60 Identification Marking Surface
70 Retaining Strap Member
75 First End of Retaining Strap Member
80 Second End of Retaining Strap Member
85 Strap Member Fastener
90 Fastener Accepting Aperture
100 Fastening and Identification Device
110 Planar Support Member
115 Top Side of Support Member
120 Bottom Side of Support Member
125 Hook and Loop Strap Members
130 First End of Strap Members
135 Second End of Strap Members
A Longitudinal Cylindrical Axis of Fastener Member
B Longitudinal Bore Axis of Tube Holding Member

Construction

Figure 1:
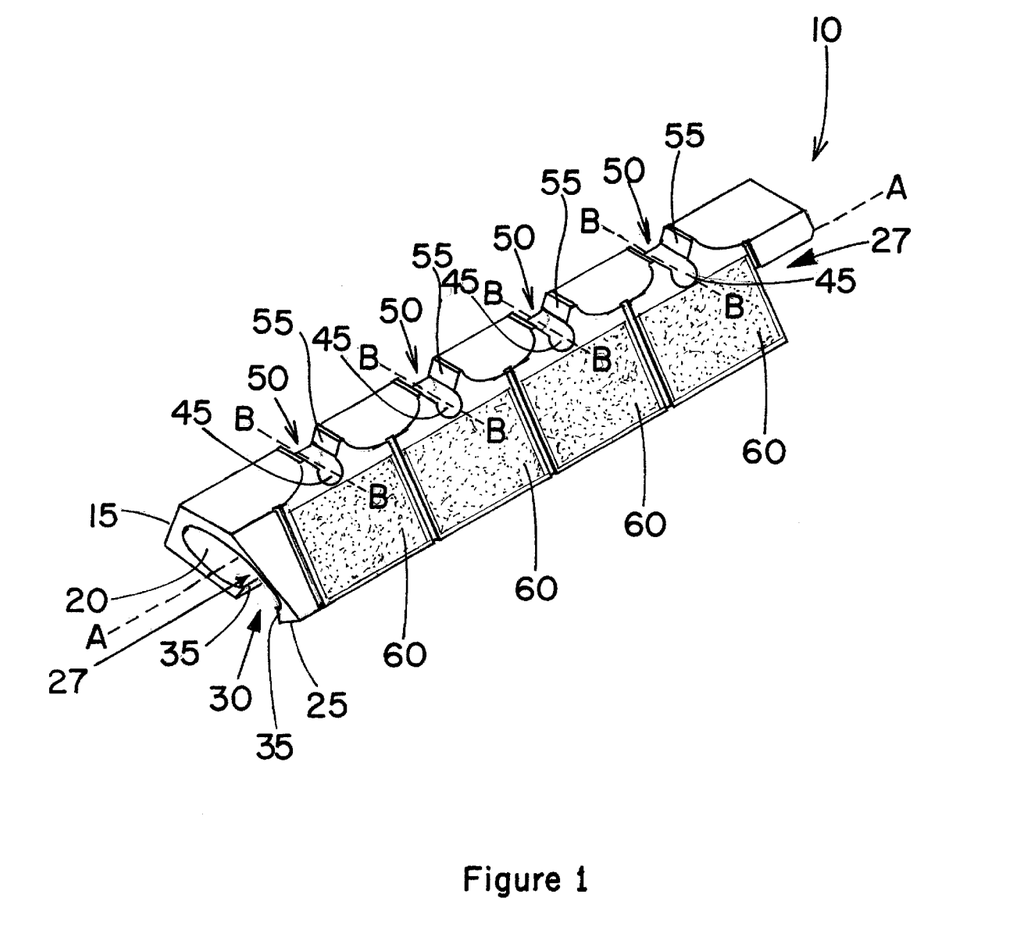
FIG. 1 is a perspective view of a preferred embodiment of the fastening and identification device of the present invention.
Figure 2:
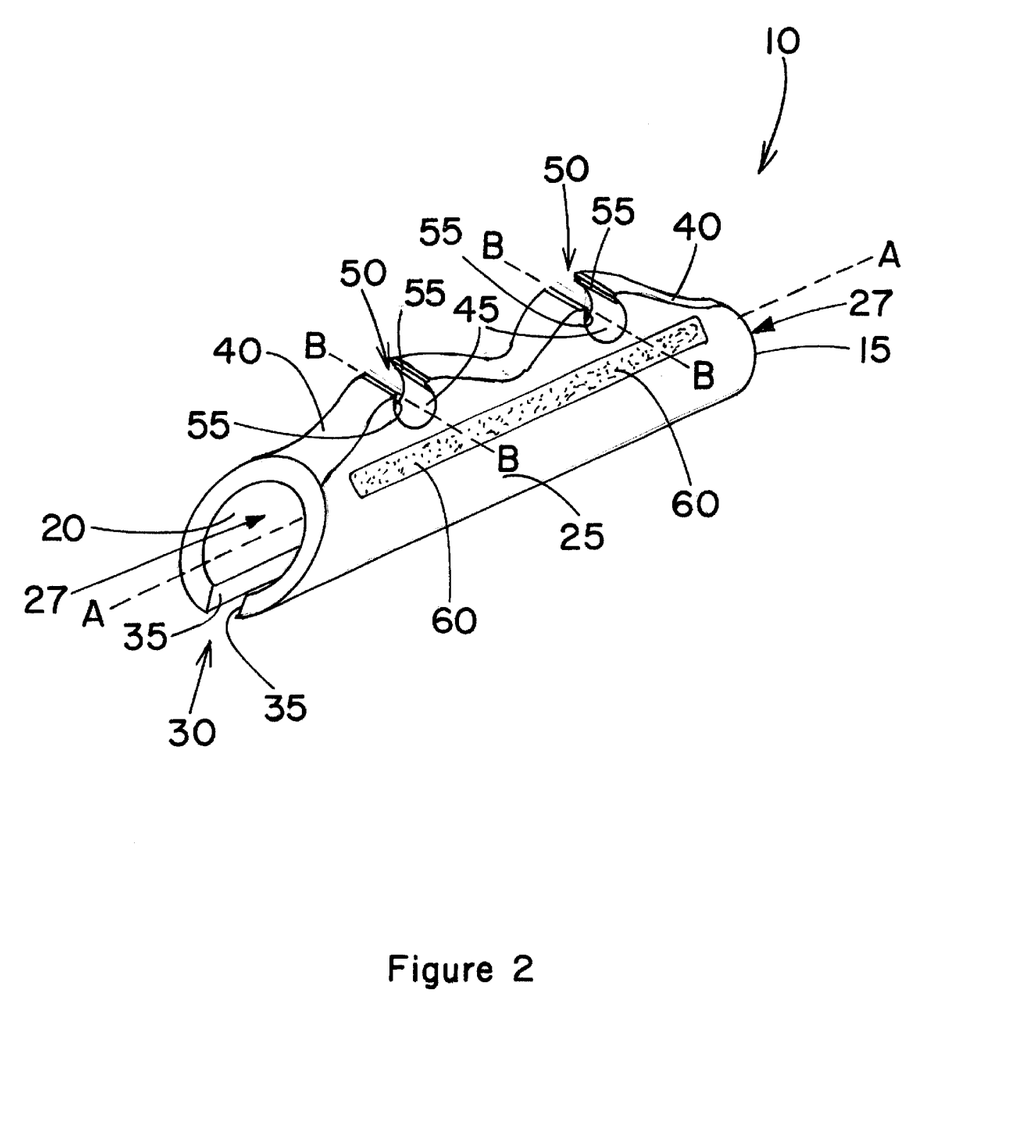
FIG. 2 is a perspective view of another embodiment of the fastening and identification device of the present invention.

Referring to FIGS. 1 and 2, the preferred embodiments of the intravenous administration lines fastening and identification device 10 is shown. The device 10 includes an open ended hollow cylindrical fastening member 15 of resilient, flexible, polymeric, resinous material. The cylindrical member 15 has an inner surface 20 and an outer surface 25, and includes a cylindrical bore 27 having a longitudinal cylindrical axis A there through. The cylindrical member 15 has a full length longitudinal slit aperture 30 produced by removing a small angle arc section from the total length of the cylindrical member 15 to access the cylindrical bore 27. This produces a longitudinal slit aperture 30 with beveled edges 35 resulting in the slit aperture 30 decreasing in width from the outer surface 25 of the fastening member 15 to the inner surface 20. The beveled edges 35 of the fastening member slit aperture 30 allows facile mounting and demounting of the device 10 to or from a linear support.

A plurality of tube holding members 40, also of resilient, flexible, polymeric, resinous material, and each with a cylindrical bore 45 and longitudinal bore axis B, are secured to the outer surface 25 of the hollow cylindrical fastening member 15 opposite the fastening member longitudinal slit aperture 30. Each tube holding member 40 is secured such that the longitudinal bore axis B is oriented perpendicular to the longitudinal cylindrical axis A of the fastening member 15. The tube holding members 40 each have a full length longitudinal slit aperture 50 positioned opposite the fastening member 15, with the slit aperture 50 accessing the tube holding member cylindrical bore 45. Again, this full length longitudinal slit aperture 50 is produced by removing a small angle arc section from the total length of the tube holding member 40. This produces a longitudinal slit aperture 50 with beveled edges 55 resulting in the slit aperture 50 decreasing in width from the outer surface of the tube holding member 40 to the cylindrical bore 45. In one embodiment, the tube holding member 40 is generally cylindrical in shape with a centered cylindrical bore 45, as shown in FIG. 1. In another embodiment, the tube holding member 40 is generally triangular in shape with one side secured to the fastening member 15, and the cylindrical bore 45 positioned near one apex of the triangle opposite the one side secured to the fastening member 15, as shown in FIG. 2.

An identification marking surface 60 is present on the cylindrical fastening member outer surface 20. The marking surface 60 is positioned in register with and adjacent to each tube holding member 40 secured to the cylindrical fastening member 15, as depicted in FIGS. 1 and 2. The identification marking surface 60 is suitable for receiving notation from a writing instrument, such as a pen or permanent marker.

In use, the fastening and identification device 10 is fastened to a bed rail or wheel chair arm by positioning the longitudinal slit aperture 30 of the hollow cylindrical fastening member 15 above and parallel to the rail or arm and applying a downward force. The resilient flexible polymeric resinous material of the device 10 is sufficiently flexible to allow the fastening member 15 to open at the slit aperture 30 and accept the rail or arm into the hollow interior of the fastening member 15. The fastening member 15 is sufficiently resilient to securely hold the device 10 to the bed rail or other similar structure. The flexibility of the fastening member 15 is sufficient to accommodate a variety of different size and shape rails, post or other similar structures, including cylindrical or square supports.

An intravenous tube line is then secured within the cylindrical bore 45 of a tube holding member 40. The IV tube line is positioned in the longitudinal slit aperture 50 of the tube holding member 40 and slight downward pressure is applied. The resilient flexible polymeric resinous material of the device 10 is sufficiently flexible to allow the tube holding member 40 to open at the slit aperture 50 and accept the IV tube line into the cylindrical bore 45 of the tube holding member 40. The cylindrical bore 45 is sized to be slightly larger than standard IV tube lines, thereby allowing the IV line to slide through the bore 45 with minimum effort. However, there is sufficient friction between the IV tube line and the bore interior surface of the tube holder member 40 to prevent undue slippage of the IV tube line. The beveled edge 55 of the slit aperture 50 described above also prevents the IV tube line from inadvertently escaping from the tube holding member 40.

The device 10 is fabricated with a plurality of tube holding members 40 present. The device of FIG. 2 has two tube holding members 40, while the device 10 of FIG. 1 has four tube holding members 40. Greater numbers of tube holding member 40, such as three, five or six, may be present in the device 10 as well. To secure a large number of IV tube lines, it may be useful to combine two or more devices 10 to maintain the IV tube lines in order. Each tube holding member 40 has a corresponding identification marking surface 60 present on the cylindrical fastening member outer surface 25. The marking surface 60 is suitable for receiving notation identifying the contents of the IV tube line held in the corresponding tube holding member 40. Thus, the care giver can easily identify which IV tube line carries a particular medication.

A further advantage of the disclosed device 10 is the easy and quick transfer of the fastening and identification device 10 from, for instance, a bed rail to an IV tree hanger when transport or ambulation of the patient is desired. The flexible resilient character of the device 10 allows removal of the device and the associated IV tubing lines from one support by simple upward force, and reconnecting the device 10 to another similar support, again with mild force application.

The fastening and identification device 10 of the present invention is contemplated as being fabricated from a suitable polymeric resin material and formed by an injection molding process. Next, the device 10 has the identification marking surface 60 secured in position, then the whole device 10 is sealed in a protective bag. The bag and contained device 10 may optionally be sterilized. The device 10 can be removed from the bag at the point of use and, when no longer needed, disposed of as a non-biohazardous material in the trash.

Figure 3:
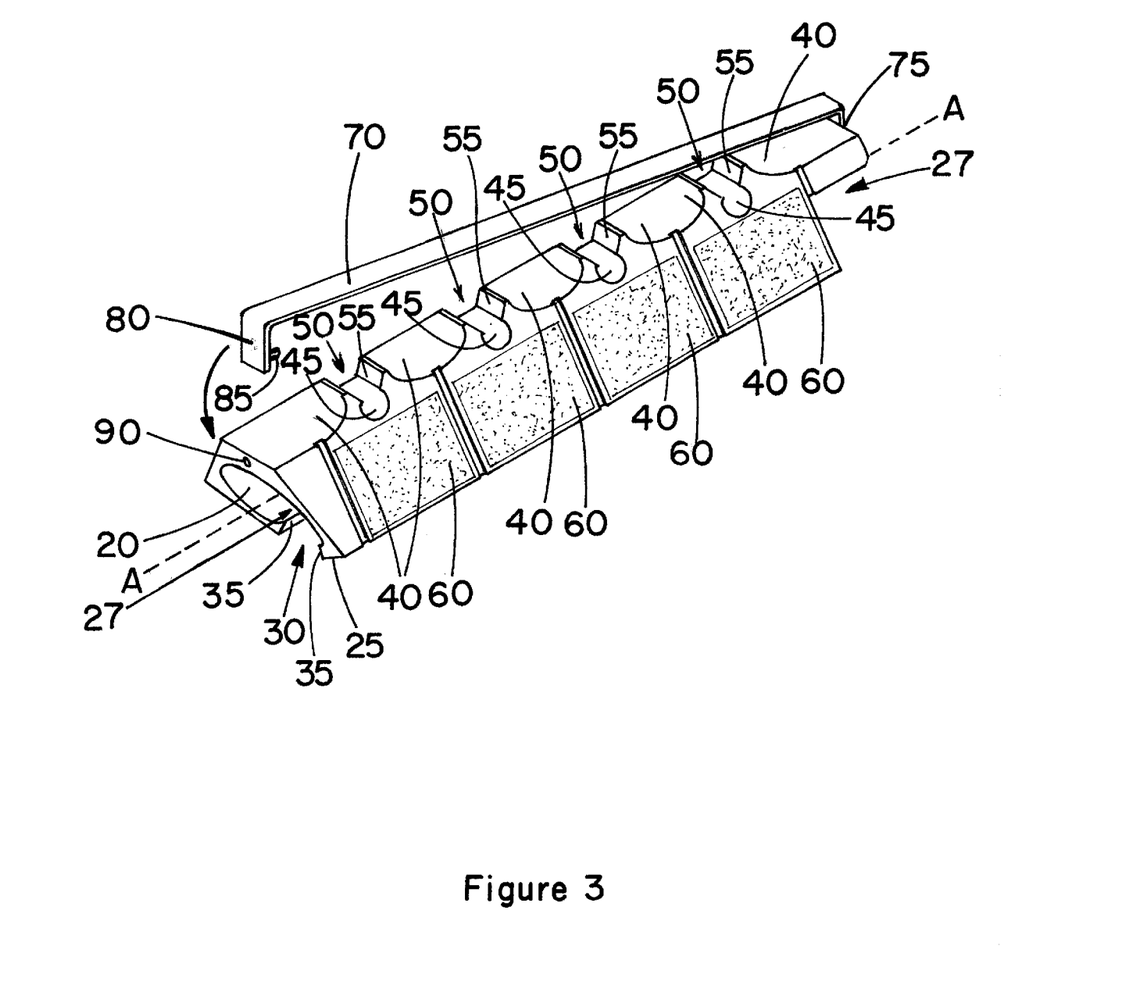
FIG. 3 is a perspective view of a further embodiment of the fastening and identification device of the present invention.

Referring now to FIG. 3, a further embodiment of the IV line fastening and identification device 10 is shown. Those elements of the device 10 of FIG. 3 in common with the elements of FIGS. 1 and 2 are given the same indica. To further ensure the secure holding of IV tube lines by the tube holding members 40, a retraining strap member 70 is provided. The strap member 70 is permanently affixed at a strap member first end 75 to one end of the cylindrical fastening member 15. The strap member 70 extends from the affixed first end 75 over the slit apertures 50 of all tube holding members 40 present in the device 10. The second end 80 of the strap member 70 contains a fastener member 85 designed to reversibly secure the strap member second end 80 to the end of the cylindrical fastening member 15 opposite the end where the strap member 70 is permanently affixed. The fastener member 85 fits reversibly into an aperture 90 on the end of the cylindrical fastening member 15, thereby reversibly securing the strap member 70 over the slit apertures 50 of all tube holding members 40 present. In use, the retaining strap member 70 pivots at the permanently affixed strap member first end 75 to move the retaining strap member 70 away from the slit apertures 50, allowing insertion of the IV tubing into the cylindrical bore 45 of the tube holding members 40. The retraining strap member 70 then pivots to secure the strap member 70 over the slit apertures 50.

Figure 4:
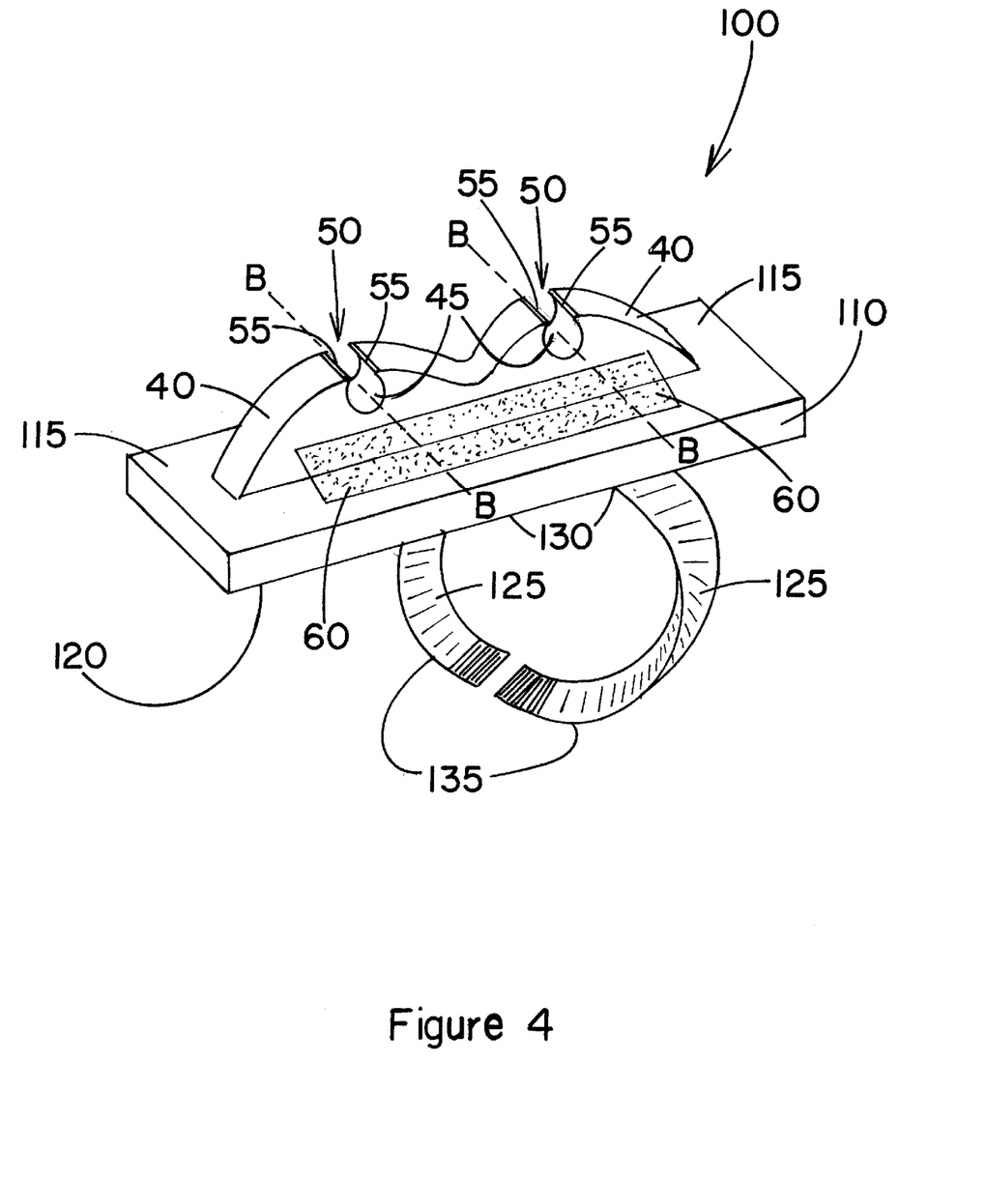
FIG. 4 is a perspective view of an alternative embodiment of the fastening and identification device of the present invention.

Referring now to FIG. 4, an alternative embodiment of the IV line fastening and identification device 100 is shown. Those elements of the device 100 of FIG. 4 in common with the elements of FIGS. 1–3 are given the same indica. The device 100 includes a generally planar support member 110 of resilient, flexible, polymeric, resinous material, the support member 110 having a top side 115 and a bottom side 120. A plurality of tube holding members 40, also of resilient, flexible, polymeric, resinous material, and each with a cylindrical bore 45 and longitudinal bore axis B, are secured to the top side 115 of the support member 110. The tube holding members 40 each have a full length longitudinal slit aperture 50 positioned opposite the support member 110, with the slit aperture 50 accessing the tube holding member cylindrical bore 45. Again, this full length longitudinal slit aperture 50 is produced by removing a small angle arc section from total length of the tube holding member 40. This produces a longitudinal slit aperture 50 with beveled edges 55 resulting in the slit aperture 50 decreasing in width from the outer surface of the tube holding member 40 to the cylindrical bore 45. The longitudinal bore axis B of the cylindrical bore 45 of all tube holding members 40 are mutually parallel.

An identification marking surface 60 is present on the top side 115 of the support member 110. The marking surface 60 is positioned in register with and adjacent to each tube holding member 40 secured to the top side 115 of the support member 110. The identification marking surface 60 is suitable for receiving notation from a writing instrument, such as a pen or permanent marker.

Figure 5:
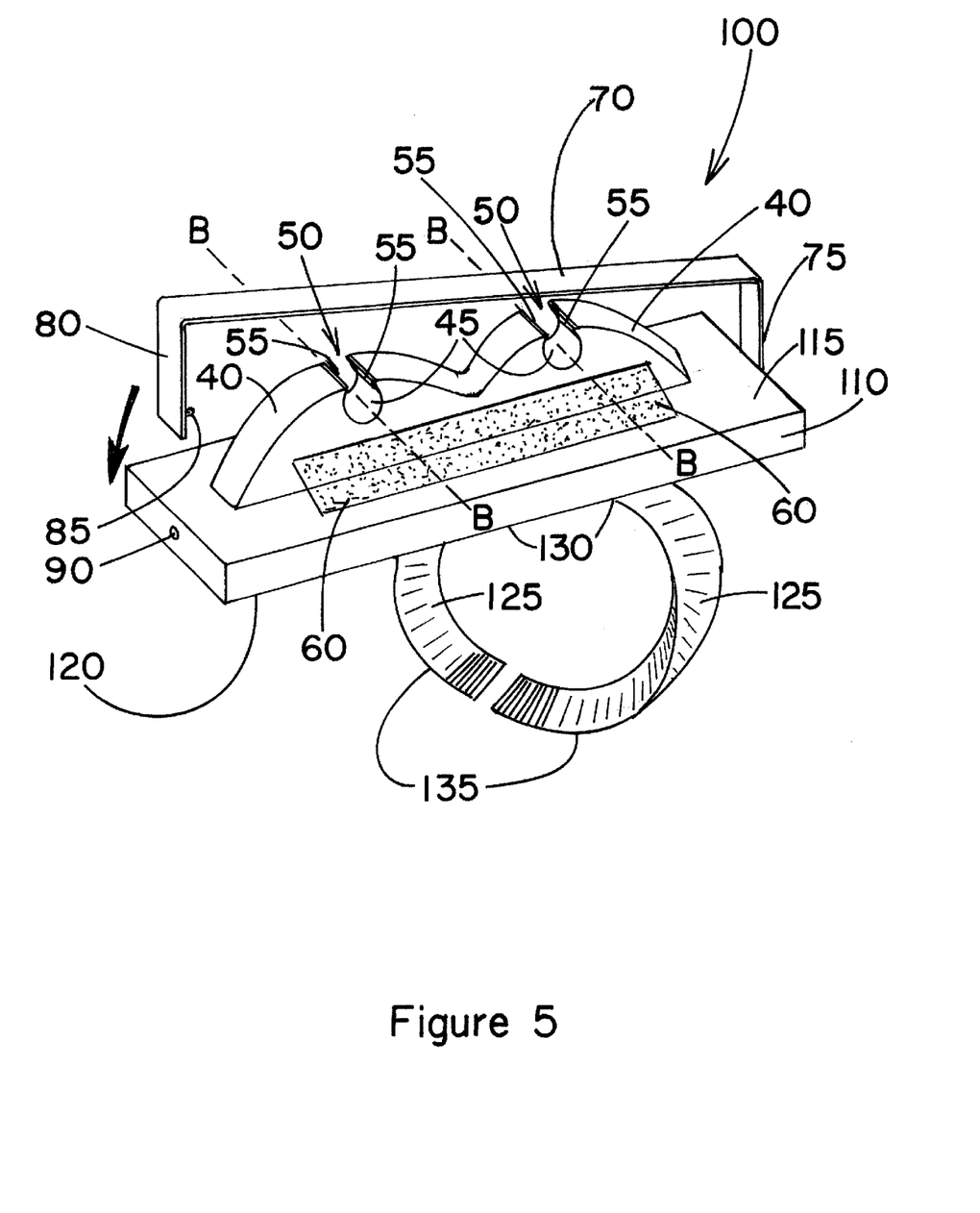
FIG. 5 is a perspective view of a further alternative embodiment of the fastening and identification device of the present invention.

A pair of hook and loop fastener straps 125 are secured at a first end 130 to the bottom side 120 of the support member 110. The straps 125 are of sufficient length to encircle a human limb, such as an arm or leg, and are readily connected and disconnected at a second end 135 to secure the device 100 in place. FIG. 4 shows the tube holding member 40 as triangular members with one side secured to the support member 110, and the cylindrical bore 45 positioned near one apex of the triangle opposite the one side secured to the support member 110. Alternatively, the tube holding members 40 may be cylindrical in shape with a central cylindrical bore 45 for accepting IV tubing as depicted in FIGS. 1 and 3. To further ensure the secure holding of IV tube lines by the tube holding members 40, a retraining strap member 70 is provided for the device 100, as shown in FIG. 5. The strap member 70 is permanently affixed at a strap member first end 75 to one end of the planar fastening member 110. The strap member 70 extends from the affixed first end 75 over the slit apertures 50 of all tube holding members 40 present in the device 100. The second end 80 of the strap member 70 contains a fastener member 85 designed to reversibly secure the strap member second end 80 to the end of the planar fastening member 110 opposite the end where the strap member 70 is permanently affixed. The fastener member 85 fits reversibly into an aperture 90 on the opposite end of the planar fastening member 110, thereby reversibly securing the strap member 70 over the slit apertures 50 of all tube holding members 40 present. The number of tube holding members 40 of the device 100 preferably ranges from two to six, although larger numbers are contemplated.

The present device 100 is also employed to maintain and identify IV tubing lines when transport or ambulation of the patient receiving the IV medication is desired. The device 100, containing the several IV tubing lines, is secured to the patient's limb. The IV supply containers can then be readily transported with the patient without tangling of the IV tube lines.

While the invention has been particularly shown and described with reference to preferred embodiments thereof, it will be understood by those skilled in the art that various changes in form and details may be made therein without departing from the spirit and scope of the invention.

I claim:

1. An intravenous administration lines fastening and identification device comprising;
    (a) a hollow cylindrical fastening member of resilient flexible polymeric resinous material, said cylindrical member having inner and outer surfaces and a cylindrical bore with longitudinal cylindrical axis there through, said cylindrical member having a full length longitudinal slit aperture therein accessing said cylindrical bore;
    (b) a plurality of tube holding members of resilient flexible polymeric resinous material, said tube holding members each with cylindrical bore and longitudinal bore axis there through, said each tube holding member secured to the outer surface of said hollow cylindrical fastening member opposite said longitudinal slit aperture, said each tube holding member longitudinal bore axis oriented perpendicular to said fastening member longitudinal cylindrical axis, said each tube holding member having a full length longitudinal slit aperture opposite said fastening member, said slit aperture accessing said tube holding member cylindrical bore; and
    (c) an identification marking surface on said cylindrical fastening member outer surface in register with and adjacent said each tube holding member secured thereto.

2. The device according to claim 1 wherein said fastening member slit aperture has beveled edges adapted for facile mounting and demounting of said fastening and identification device.

3. The device according to claim 1 wherein said each tube holding member slit aperture has beveled edges adapted for facile insertion into and removal of tubing from said cylindrical bore of said each tube holding member.

4. The device according to claim 1 wherein said each tube holding member is cylindrical in shape with a central axial bore there through.

5. The device according to claim 1 wherein said each tube holding member is triangular in shape with one side secured to the fastening member, the triangular tube holding member having an axial bore adjacent an apex of the triangular tube holding member opposite the one side secured to the fastening member.

6. The device according to claim 1 further including retaining means reversibly fastenable across the plurality of said tube holding members slit apertures to secure tubing within said cylindrical bore of said each tube holding member.

7. The device according to claim 6 wherein said retaining means includes a strap member permanently affixed at a first end to said hollow cylindrical fastening member and reversibly fastenable at a second end to said hollow cylindrical fastening member, said strap member adapted for positioning across said each tube holding member slot aperture.

8. An intravenous administration lines fastening and identification device comprising;
    (a) a hollow cylindrical fastening member of resilient flexible polymeric resinous material, said cylindrical member having inner and outer surfaces and a cylindrical bore with longitudinal cylindrical axis there through, said cylindrical member having a full length longitudinal slit aperture with beveled edges therein accessing said cylindrical bore, the beveled edge slit aperture of the fastening member adapted for facile mounting and demounting thereof;
    (b) a plurality of tube holding members of resilient flexible polymeric resinous material, said tube holding members each with cylindrical bore and longitudinal bore axis there through, said each tube holding member secured to the outer surface of said hollow cylindrical fastening member opposite said longitudinal slit aperture, said each tube holding member longitudinal bore axis oriented perpendicular to said fastening member longitudinal cylindrical axis, said each tube holding member having a full length longitudinal slit aperture with beveled edges opposite said fastening member, said slit aperture accessing said tube holding member cylindrical bore, the beveled edge slit aperture of the tube holding member adapted for facile insertion and removal of tubing from said cylindrical bore of each tube holding member;
    (c) an identification marking surface on said cylindrical fastening member outer surface in register with and adjacent said each tube holding member secured thereto; and
    (d) retaining means reversibly fastenable across the plurality of said tube holding members slit apertures to secure tubing within said cylindrical bore of said each tube holding member.

9. The device according to claim 8 wherein said each tube holding member is cylindrical in shape with a central axial bore there through.

10. The device according to claim 8 wherein said each tube holding member is triangular in shape with one side secured to the fastening member, the triangular tube holding member having an axial bore adjacent an apex of the triangular tube holding member opposite the one side secured to the fastening member.

11. The device according to claim 8 wherein said retaining means includes a strap member permanently affixed at a first end to said hollow cylindrical fastening member and reversibly fastenable at a second end to said hollow cylindrical fastening member, said strap member adapted for positioning across said each tube holding member slot aperture.

12. An intravenous administration lines fastening and identification device comprising;

(a) a planar fastening member of resilient flexible polymeric resinous material, said planar fastening member having top and bottom surfaces;

(b) a plurality of tube holding members of resilient flexible polymeric resinous material, said tube holding members each with cylindrical bore and longitudinal bore axis there through, said each tube holding member secured to the top surface of said planar fastening member, said longitudinal bore axis of all tube holding member cylindrical bores oriented mutually parallel, said each tube holding member having a full length longitudinal slit aperture opposite said fastening member, said slit aperture accessing said tube holding member cylindrical bore;

(c) an identification marking surface on said planar fastening member top surface in register with and adjacent said each tube holding member secured thereto; and (d) a pair of hook and loop fastener tape strap members, each strap member with first and second ends, each strap member first end secured to the bottom surface of said fastening member, the strap members adapted for encircling the limb of a patient and securing the fastening and identification device thereto by joining the strap members second ends.

13. The device according to claim 12 wherein said each tube holding member slit aperture has beveled edges adapted for facile insertion into and removal of tubing from said cylindrical bore of said each tube holding member.

14. The device according to claim 12 wherein said each tube holding member is cylindrical in shape with a central axial bore there through.

15. The device according to claim 12 wherein said each tube holding member is triangular in shape with one side secured to the fastening member, the triangular tube holding member having an axial bore adjacent an apex of the triangular tube holding member opposite the one side secured to the fastening member.

16. The device according to claim 12 further including retaining means reversibly fastenable across the plurality of said tube holding members slit apertures to secure tubing within said cylindrical bore of said each tube holding member.

17. The device according to claim 16 wherein said retaining means includes a strap member permanently affixed at a first end to a first end of said planar fastening member and reversibly fastenable at a second end to a second end of said planar fastening member, said strap member adapted for positioning across said each tube holding member slot aperture.

* * * * *